(12) United States Patent
Wolfe et al.

(10) Patent No.: US 7,109,162 B2
(45) Date of Patent: Sep. 19, 2006

(54) PLANT DERIVED ANTIOXIDANTS

(75) Inventors: N. Lee Wolfe, Athens, GA (US);
Neeraj Datta, Athens, GA (US)

(73) Assignee: World Resourses Corporation, Hot Springs, AR (US)

( * ) Notice: Subject to any disclaimer, the term of this patent is extended or adjusted under 35 U.S.C. 154(b) by 31 days.

(21) Appl. No.: 10/343,771

(22) PCT Filed: Jul. 31, 2001

(86) PCT No.: PCT/US01/23988

§ 371 (c)(1),
(2), (4) Date: Jun. 25, 2003

(87) PCT Pub. No.: WO02/09646

PCT Pub. Date: Feb. 7, 2002

(65) Prior Publication Data

US 2004/0023804 A1 Feb. 5, 2004

Related U.S. Application Data

(60) Provisional application No. 60/221,755, filed on Jul. 31, 2000.

(51) Int. Cl.
*A61K 36/00* (2006.01)
*C07K 1/02* (2006.01)

(52) U.S. Cl. .......................... 514/2; 530/370; 530/300; 530/334; 530/333

(58) Field of Classification Search ............... 514/2; 530/300, 370, 334, 333
See application file for complete search history.

(56) References Cited

U.S. PATENT DOCUMENTS 5,886,156 A 3/1999 McLean et al.

FOREIGN PATENT DOCUMENTS

| WO | WO 98/11136 | 3/1998 |
| WO | WO 00/33667 | 6/2000 |

OTHER PUBLICATIONS

Attachment 1, <psyche.edu/shaun/SBlack/aagrease.html>, Apr. 22, 2005, p. 1.*
Attachment 2, <stingray.bio.cmu.edu/~web/sbio00abs_2/node5.html>, Apr. 22, 2005, pp. 1-2.*
Pip, E. et al., "Aquatic macrophytes in Shoal Lake (Manitoba-Ontario) I. Diversity, biomass and metabolic status in relation to water depth and light intensity": *Arch. Hydrobiol.Suppl. 76*, 1987 m oo, 197-222.
Chen, Hua-Ming, et al., "Antioxidant Activity of Designed Peptides Based on the Antioxidant Peptide Isolated from Digests of a Soybean Protein", *i. Agric. Food Chem.*, (1996) vol. 44, pp. 2619-2623.

* cited by examiner

*Primary Examiner*—Jon Weber
*Assistant Examiner*—Samuel W. Liu

(57) ABSTRACT

The present invention relates to a purified antioxidant polypeptide, a method of isolating and purifying said polypeptide, and method of enhancing antioxidant properties of a composition comprising addition of said polypeptide to the composition. The antioxidant is formulated alone as a nutritional supplement or is combined with other consumable products, such as foods, beverages, vitamins, herbal extracts, or other antioxidants. The present invention also relates to methods for identifying and quantifying the antioxidant polypeptide in food and beverages.

15 Claims, 1 Drawing Sheet

PLANT DERIVED ANTIOXIDANTS

This application is a national stage entry under 35 U.S.C. 371 of PCT patent Application No. PCT/US01/23988 filed on Jul. 31, 2001, which priority to provisional Application No. 60/221,755 filed on Jul. 31, 2000.

TECHNICAL FIELD

The present invention relates to antioxidants obtained from plant sources, assays for determining the presence of the antioxidants in foods, nutritional compositions containing the antioxidants and other uses of the antioxidants.

BACKGROUND OF THE INVENTION

The characterization and marketing of naturally occurring antioxidants is receiving widespread attention in the everyday lives of many people today. Certain food groups having high levels of antioxidants are believed to provide prophylactic health benefits. Therefore, a myriad of supplements, herbal formulations, and herbal extracts are being marketed to consumers. In many cases, these "elixirs" are sold without solid scientific foundation. Currently, there is increased scientific interest in the role of antioxidants and the part they play in human health by reducing excessive free radicals.

Free radicals are oxygen atoms that contain unpaired hydrogen electrons. Free radicals are very unstable and react quickly with other compounds, trying to capture the needed electron to gain stability. Generally, free radicals attack the nearest stable molecule and grab its electron. When the attacked molecule loses an electron, it becomes a free radical itself, beginning a chain reaction. Once the process is started it can cascade, finally resulting in the disruption of a living cell.

Some free radicals arise normally during metabolism. For example, the immune system cells of the body purposely create free radicals to neutralize viruses and bacteria. However, environmental factors such as pollution, radiation, cigarette smoke and herbicides can result in the production of an excessive amount of free radical formation.

Normally, the body can accommodate free radicals. However, if antioxidants are unavailable or the free radical production becomes excessive, damage can occur. It is well known that free radical damage accumulates with age.

Many free radical supplements, based on natural food stuffs, herbal ingredients, herbal extracts and formulations thereof, are available on the market. These supplements allegedly contain components that somehow either prevent the formation of or quickly react with the chemically reactive free radical species such as singlet oxygen, peroxides, and the hydroxy free radicals.

Three highly touted antioxidants, vitamin C, vitamin E, and beta-carotene, and their role as antioxidants have received high scientific scrutiny. These antioxidants are abundant in foodstuffs associated with good health and are readily available over the counter as dietary supplements. Chemically they are known to react with molecular oxygen and with other selected free radicals. These antioxidants provides a source of electrons to the reactive radical thus terminating the propagation step and intercepting the free radical before it can react with other biological molecules. The exact mechanism of how these compounds operate as scavengers of free radicals in the body is not known. Other classes of antioxidants include the flavenoids, isoflavenoids, and other natural occurring compounds that contain reactive phenolic groups.

Scientists have devised some tests to measure the effectiveness with which antioxidants react with free radicals. These assays are generally based on the reaction of free radicals such as peroxides, singlet oxygen, or hydroxy radicals with free radical inhibitors. However, the isolation of additional antioxidants and the ability to rapidly and reliably testing foods or nutritional substances for the presence of antioxidants is lacking.

Therefore, there is a need for the identification and isolation of additional antioxidants so that nutritional supplements containing the antioxidants can be made available to health conscious consumers or individuals particularly susceptible to the accumulation of excessive free radicals. There is also a need for antioxidants for use in removing oxidants from various substances, such as tobacco products. Reliable methods for determining whether a particular food or nutritional substance contains the desired antioxidants are also needed.

SUMMARY OF THE INVENTION

The isolation, characterization, and use of a highly potent antioxidant is described herein. This antioxidant has been isolated from plants and is found in selected foods. This naturally occurring antioxidant reacts with anthropogenic chemical carcinogens and teratogens to produce non-toxic products. The chemistry of the antioxidant has been studied in detail under controlled reaction conditions. Furthermore, reactions of the antioxidant have been studied in whole plant systems where they are shown to be effective. The antioxidant is formulated alone as a nutritional supplement or is combined with other consumable products, such as foods, beverages, vitamins, herbal extracts, tobacco and its byproducts, or with other antioxidants. Methods for identifying and quantifying the antioxidant in food and beverages are also provided. The antioxidant of the present invention may also be used in cosmetic products and pharmaceutical products.

Scientific information on the chemical stability and chemical reactions of this antioxidant is provided herein. The activity of this component in selected foods, beverages and nutritional supplements is described.

It is therefore an object of the present invention to provide a new isolated antioxidant.

Accordingly, it is an object of the present invention to provide the characterization of a new isolated antioxidant.

It is another object of the present invention to provide a method for determining which foods and beverages have optimal antioxidant capacities.

It is yet another object of the present invention to provide a nutrient supplement useful for reducing excessive free radical accumulation.

It is further an object of the present invention to provide new uses for the antioxidant composition of the present invention, including but not limited to use in pharmaceutical compounds, cosmetic compounds and in filters for tobacco smoke.

These and other objects, features and advantages of the present invention will become apparent after a review of the following detailed description of the disclosed embodiments and the appended claims.

DETAILED DESCRIPTION OF THE INVENTION

Figure 1:
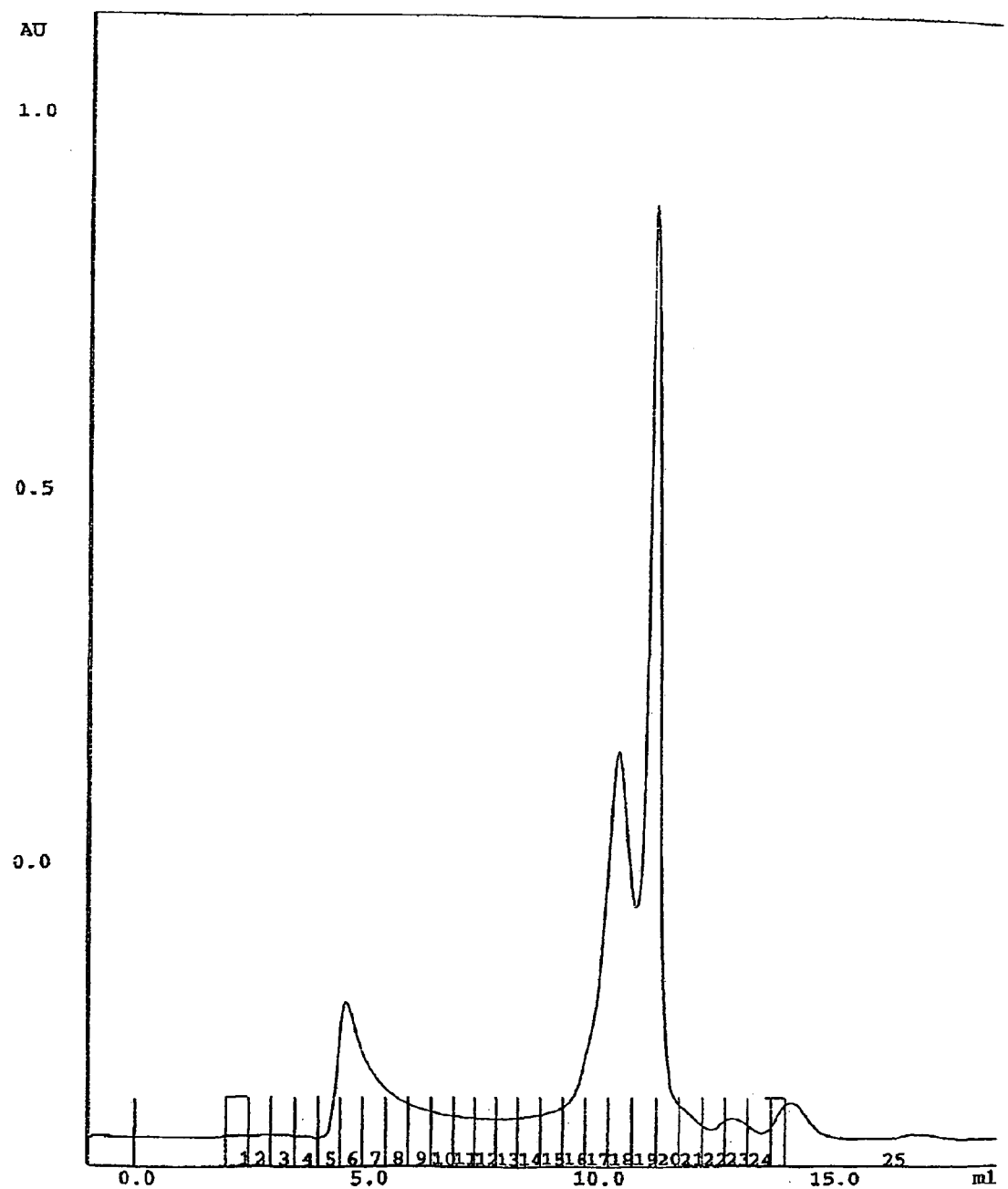
FIG. 1 is an FPLC chromatogram of a plant extract.

A new and unique strong antioxidant composition, isolated from selected plants and foods is described herein. Based on the partial characterization of the compound, the antioxidant composition is tentatively identified as a peptide. The antioxidant composition functions as a reducing agent, or electron mediator, and requires an electron source such as vitamin C to be effective. For example the antioxidant composition potentiates vitamin C as an antioxidant. This antioxidant composition may be the unknown factor in antioxidant research and could actually be the ultimate antioxidant often associated with vitamin C. The antioxidant composition has commercial value for promoting and marketing products in the wine or juice industry and in the health supplement or herbal industry as shown by the findings below. In isolated form, the antioxidant composition also has value as a food additive and as an over-the-counter natural antioxidant or herbal antioxidant. The antioxidant composition also may remove oxidants from tobacco products, such as smoke. Further, the composition has antioxidant value when added to pharmaceuticals or cosmetics.

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In one embodiment, the present invention provides the partial characterization of an isolated peptide from Elodea as SEQ ID NO:1 as described in the Examples.

SEQ ID NO: 1 Met Pro Leu X Glu Lys Asp X/Gly Ala Thr/Lys X X.

It is to be understood that X in SEQ ID NO: 1 may be any naturally occurring amino acid. In a preferred embodiment, one or more Xs is a methionine. The designations X/Gly and Thr/Lys indicate that either X or Gly, or Thr or Lys may be present at the indicated positions.

Met Pro Leu X Glu Lys Gly Leu Asp Gly    SEQ ID NO: 2
Ala Thr/Lys X X.

Met Pro Leu X Glu Lys Gly Leu Asp        SEQ ID NO: 3
X/Gly Ala Lys X X.

Met Pro Leu X Glu Lys Gly Leu Asp        SEQ ID NO: 4
X/Gly Ala Thr X X.

Met Pro Leu X Glu Lys Gly Leu Asp Gly    SEQ ID NO: 5
Ala Thr X X.

Met Pro Leu X Glu Lys Gly Leu Asp Gly    SEQ ID NO: 6
Ala Lys X X.

Met Pro Leu X Glu Lys Gly Leu Asp X/Gly  SEQ ID NO: 7
Ala Thr/Lys X X.

It is to be understood that X in SEQ ID NO: 2–7 may be any naturally occurring amino acid. In a preferred embodiment, one or more Xs is a methionine. Further, it is to be understood that when the antioxidants of the present invention are peptides, as described in the preferred embodiments shown in SEQ ID Nos: 1 to 7, that conservative amino acid substitutions may be made for any of these amino acids, as outlined in the conservative amino acid substitutions shown above.

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the peptides described herein. Techniques for solid phase synthesis are known to those skilled in the art.

Alternatively, the peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide and, if required, renaturing the peptide. Techniques sufficient to guide one of skill through such procedures are found in the literature.

When several desired peptides are encoded in the nucleotide sequence incorporated into a vector, one of skill in the art will appreciate that the peptides may be separated by a spacer molecule such as, for example, a peptide, consisting of one or more amino acids. Generally, the spacer will have no specific biological activity other than to join the desired peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant peptide may be built into the vector. Such sequences are known in the art. For example, a nucleotide sequence encoding for a poly histidine sequence may be added to a vector to facilitate purification of the expressed recombinant peptide on a nickel column.

Once expressed, recombinant peptides, can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents. Other degrees of homogeneity may be useful for use in cosmetics.

One of skill in the art will recognize that after chemical synthesis, biological expression or purification, the desired peptides may possess a conformation substantially different than the native conformations of the peptides. In this case, it is often necessary to denature and reduce the peptide and then to cause the peptide to re-fold into the preferred conformation. Methods of reducing and denaturing peptides and inducing re-folding are well known to those of skill in the art.

The peptide is isolated from plants such as the Elodea plant (*Elodea canadensis*) as described below in more detail in the Examples. The antioxidant peptide is heat stable, has broad pH stability, and is protease resistant. It is soluble in methanol, active both in aerobic and anaerobic conditions and has a broad substrate specificity with a pH optima of pH 8.5.

Calibration of SUPERDEX peptide chromatography column gave a molecular weight for this peptide of approximately 1.2 KDa. The UV-V is for this peptide showed absorption maxima at 216 and 270 nm. The purified fraction exhibited the ability to degrade compounds such as perchloroethylene (PCE), trichloroethylene (TCE), pentachlorophenol (PCP), 1,2-dichloro-4-(3,4-dichlorophenyl)-benzene (TCB), 2,6-dichlorobenzamide (DCB), 7-chloro-4-dimethylamino-3,6,10,12,12a-pentahydroxy-6-methyl-1,11-dioxo-4,4a,5,5a,6,12a-hexahydrotetracene-2-carboxamide (CTC), toxaphene, and 1-chloro-4-[2,2,2-trichloro-1-(4-chlorophenyl)-ethyl]-benzene (DDT). The activity of the peptide is completely inhibited by ethylenediamine-tetraacetic acid (EDTA) and requires ascorbate as the electron donor.

The antioxidant is present in and can be isolated from many other plants besides Elodea. In fact, it has been found, in varying quantities, in most of the plants analyzed. For example, the peptide is present in high concentrations in hay. With the amino acid sequence of this peptide in hand, three methods for scaling up the manufacturing of the peptide will be available: (1) by the conventional method which is extraction from plants with high activity and ready availability, for example hay; (2) chemical syntheses (this should be the cheapest and the fastest method to produce it in bulk, however, if the peptide is glycosylated (has a sugar moiety on it) then the next method would be the most economical); and (3) expressing it as a recombinant fusion protein in yeast. In yeast, the peptide would be synthesized with the posttranslational modifications like glycosylation. This method would only be applicable if the peptide is found to have some post translational modification like glycosylation.

Antioxidant activity is usually associated with the destruction of free radicals—species that are quite reactive by themselves. The fact that the antioxidant component described herein is such a strong antioxidant—strong enough to reduce chlorinated hydrocarbons in water, a feat that is very hard to do—offers great potential, maybe even a new paradigm in healthy foods and food additives as well as other commercial uses.

For example, the peptide is added to liquids, such as water, milk, juice, coffee or tea or is incorporated in a commercially available or new nutrient supplement, such as a protein shake, protein shake powder, powdered egg or egg substitute, bread, soup, pudding, cereal, spice mixture or other food to which a nutrient supplement could be added.

An assay for the determination of the presence of the peptide, and therefore "antioxidant activity" is described herein in the examples. The chlorinated compound hexachloroethane (HCA) is used as the assay for activity. The relative percent disappearance of hexachloroethane is used as a measure of the activity in ground up food or liquid. The more hexachloroethane that reacts in a given increment of time, the more peptide is present. This assay is actually predicated on detailed kinetic/mechanistic studies.

By using the assay, it has been discovered that the antioxidant is present in several common food products, but not all foods. For example, it is present in red wine—thought to be rich in antioxidants—but not white wine. It is present in the skins of both white and red grapes. The difference is in the fermentation process as red wines are fermented with the skins on while white wines are not.

In addition to the use of the antioxidant of the present invention in foods and beverages, it may also be added to cosmetics or pharmaceuticals to provide antioxidant activity. The antioxidant of the present invention may also be employed to decrease the oxidative potential of tobacco byproducts, including but not limited to tobacco smoke. Such a use may include inclusion in a cigarette filter, or some other filter for smoke.

The following examples will serve better to illustrate the isolation and characteristics of the antioxidant and methods of determining the presence of the antioxidant in foods and liquids. It will be appreciated that other embodiments and uses will be apparent to those skilled in the art and that the invention is not limited to these specific illustrative examples.

EXAMPLE 1

Isolation and Characterization of the Antioxidant from the Plant, Elodea Plant Materials and Buffer Solutions Plant samples of Elodea (*Elodea canadensis*) were collected from a local lake near Athens, Ga. and washed thoroughly in running water, then were frozen in liquid nitrogen and ground in a mortar pestle to fine powder. To study the effect of elevated temperature/autoclaving on the stability of dehalogenase-like activity, plants were autoclaved for 15 minutes and used to prepare extract for activity analysis. The extraction and assay buffer was 25 mM Tris, pH 8.5+ L-ascorbic acid (final concentration of 1 mM). All the substrate (HCA, PCE, and TCE,) stocks were prepared in methanol to a stock concentration of 1 mg/ml (1000 ppm). The final concentrations, of all the substrates used in assays were 5 µg/ml (5 ppm).

Isolation and Purification:

The fresh Elodea plants were freeze dried in liquid nitrogen, ground to fine powder in mortar and pestle and stored at −70° C. Further steps of the isolation and purification were carried out at room temperature. A 100 g sample of frozen Elodea (fine powder) was homogenized to a slurry in 200 ml of buffer using a polytron. This fine slurry was filtered through 8 layers of cheesecloth and the filtrate centrifuged at 10,000 rpm for 30 minutes. The supernatant was first purified by pH precipitation. The pH was lowered to pH 2.0 with HCl to allow the precipitates to flocculate for about 4 hours at 4° C. and centrifuged as above. The pH of the supernatant was raised to 12.0 with NaOH and after another 4 hours at 4° C., it was again centrifuged for 30 minutes. The supernatant was adjusted to pH 8.5 and was concentrated 5× to 6× by boiling in a microwave.

After cooling and centrifugation as above, the supernatant was filtered through an Amicon 3K centricon filter and the filtrate was further concentrated, by boiling, to about 10× of starting volume. The resulting filtrate, a partially purified extract was used for most of the experiments described herein. For further purification, this <3K filtrate was freeze dried and resuspended in methanol, thereby removing the water soluble components. The clarified methanol solution was again lyophilized and the powder resuspended in a small volume of the 25 mM Tris-HCl buffer, pH 8.5. This was then further purified on a Pharmacia Biotech Fast Protein Liquid Chromatography (FPLC) equipped with a dual wavelength UV detector. Conditions for FPLC purification are as follows: a Superdex peptide PE 7.5/300 column; 100 ul injection volume; 25 mM Tris-HCl buffer with 150 mM NaCl, pH 8.5; 0.5 ml fractional volume; 0.28 ml/min flow rate and a UV detector at 280 nm. The FPLC chromatogram is shown in FIG. 1. Fractions 18, 19 and 20 were collected for the amino acid sequencing described below in Example 3. Using commercial standards, a plot of molecular weight versus retention times gave a linear plot. Based this plot the molecular weight was estimated to be between 800 Da and 1.5 KDa.

HCA Assays—Batch Studies

Crude and purified fractions of the Elodea extracts were assayed for activity with hexachloroethane (HCA). 2 mL of the extracts were placed in 20 mL batch centrifuge tubes and then 18 mL of 25 mM Tris buffer (pH 8.5)+0.2 mL ascorbate was added. Each vial was spiked with a stock solution of HCA to obtain a final concentration of 5 ppm and sealed immediately. Head space was minimized in all batches. The controls contained only the buffer solution, ascorbate and HCA and were prepared and handled in parallel with all samples. These experiments were performed in triplicate. The samples and their controls were incubated for different time periods ranging from 2 hours to 40 hours before analysis. At predetermined time intervals, the sample and control batch tubes were sacrificed for analysis. All samples were extracted (1:1 ratio) into the hexane phase before analysis by GC/ECD.

GC Analysis

A Hewlett Packard 5890 series-II gas chromatograph fitted with an electron capture detector and a DB-1 capillary column was used for analysis of volatile halogenated compound HCA. Column dimensions were 20 mm×0.18 mm×0.4 µm; Column phase: 100% methyl siloxane. All injections were made with an auto-injector (HP 7673) (0.5 µl volume of sample), and the solvent for all injected samples was hexane. Column temperature was initially 30° C. for 2.00 minutes, then ramped to 175° C. at 6.00° C./minute and then ramped to 275° C. at 10.0° C./minute and held for 2.00 minutes.

Homogeneous Kinetics

To assess antioxidant activity of the extract, HCA was selected as a substrate. It was chosen because it has high water solubility and good analytical sensitivity and forms intermediates that are readily analyzed by GC/ECD. Previous in vivo research suggested that the activity could be due to bacterial contamination. In order to eliminate this possibility, we decided to surface sterilize the plants before extraction. There was no significant difference in activity between extracts from surface sterilized plants with 10% bleach for 4 minutes and non-sterilized plants (data not shown). Also, the activity was maintained in extracts from autoclaved plants. This indicated that the extractable activity discussed below was derived from plants and not bacteria. The HCA transformation products were confirmed by GC/MS. The rapid dehalogenation of HCA was observed in all experiments. The rate of transformation of HCA was faster with the purified fraction than with crude fraction. The control experiments showed that a buffered solution of ascorbate without the extract were not responsible for the transformation of HCA in these experiments. A first-order decay model described the kinetic data for the plant extract and solute concentration, used in this study. The half-life was approximately 5.5 and 16 hours for the purified fraction and crude extract, respectively.

Purification

While standardizing the pH optima, it was observed that on lowering or raising the pH from the extraction pH of 8.5, there was precipitation without any loss of activity. As the activity was heat stable, boiling was used as a concentration step after the pH purification step. Further purification was carried out by gel filtration on FPLC. This active compound did not bind to ion exchange and hydrophobic interaction columns but the column was later found to be useful to remove some impurities from the partially purified fraction. After desalting, the fraction was purified on a Superdex Peptide column and new fractions were collected. A single peak eluted from the Superdex peptide column. This fraction was shown to have antioxidant (dehalogenase-like) activity. For these studies and for further characterization, it was assumed that this fraction was pure. Calibration of the Superdex peptide column gave a molecular weight for this compound of approximately 1.2 kDa. The UV-Vis for this compound showed absorption maxima at 216 and 270 nm. To determine substrate specificity, the purified fraction was tested against a series of compounds such as PCE, TCE, PCP, TCB, DCB, CTC, toxaphene and DDT. Results suggested that several of these compounds can be degraded (Table 1). The dehalogenase-like activity was also completely inhibited by 2 mM EDTA, suggesting that this component may contain one or more metals.

TABLE 1

Substrate specificity for dehalogenase-like activity extracted from Elodea plants in a 24 hr assay.

| Substrate | % Degradation |
|---|---|
| CA (Hexachloroethane) | 100 |
| PCE (Tetrachloroethylene) | 59 |
| TCE (Trichloroethylene) | 49 |
| PCP (PentachlorophenoL) | 0 |
| TCB (Trichlorobenzene) | 30 |
| DCB (Dichlorobenzene) | 16 |
| CTC (Carbon tetrachloride) | 100 |
| Toxaphene | 0 |
| DDT | 97 |

EXAMPLE 2

Isolation and Characterization of the Antioxidant from Food

Food samples were collected from a grocery store in Athens, Ga. To study the effect of high temperature/autoclaving on the stability of dehalogenase-like activity, samples of the food stuffs were autoclaved for 15 minutes and used to prepare extracts for activity analysis. The extraction and assay buffer was 25 mM Tris, pH 8.5+ L-ascorbic acid (final concentration of 1 mM). All the substrate (HCA, PCE, and TCE,) stocks were prepared in methanol to a stock concentration of 1 mg/ml (1000 ppm). The final concentrations, of all the substrates used in assays were 5 ug/ml (5 ppm).

Isolation and Purification

The isolation and purification were carried out at room temperature. A 100 ml (or 100 g sample in the case of solids) was used for the extraction. The sample was centrifuged at 10,000 rpm for 30 minutes to remove the solids. The supernatant was first purified by pH precipitation. The pH was lowered to pH 2.0 with HCl to allow the precipitates to flocculate for about 4 hours at 4° C. and centrifuged as above. The pH of the supernatant was raised to pH 12.0 with NaOH and after another 4 hours at 4° C., it was again centrifuged for 30 minutes. The supernatant was adjusted to pH 8.5 and was concentrated 5× to 6× by boiling in a microwave. After cooling and centrifugation as above, the supernatant was filtered through an Amicon 3K centricon filter and the filtrate was further concentrated, by boiling, to about 10× of starting volume. The resulting filtrate, a partially purified extract was used for most of the experiments described below. For further purification, this <3K filtrate was freeze dried and resuspended in methanol, thereby removing the water soluble components. The clarified methanol solution was again lyophilized and the powder resuspended in a small volume of the 25 mM Tris, pH 8.5 buffer. This was then further purified on a Pharmacia Biotech Fast Protein Liquid Chromatography (FPLC) equipped with a dual wavelength UV detector. Conditions for FPLC purification are as follows: a Superdex peptide PE 7.5/300 column; 100 µl injection volume; 25 mM Tris-HCl buffer with 150 mM NaCl, pH 8.5; 0.5 ml fractional volume; 0.28 ml/min flow rate and a UV detector at 280 nm.

HCA Assays—Batch Studies

Crude and purified fractions of the extracts were assayed for activity with HCA. 2 mL of the extracts were placed in 20 mL batch centrifuge tubes and then 18 mL of 25 mM Tris buffer (pH 8.5)+0.2 mL ascorbate was added. Each vial was spiked with a stock solution of HCA to obtain a final concentration of 5 ppm and sealed immediately. Head space was minimized in all batches. The controls contained only the buffer solution, ascorbate and HCA and were prepared and handled in parallel with all samples. These experiments were performed in triplicate. The samples and their controls were incubated for different time periods ranging from 2 hours to 40 hours before analysis. At predetermined time intervals, the sample and control batch tubes were sacrificed for analysis. All samples were extracted (1:1 ratio) into the hexane phase before analysis by GC/ECD.

GC Analysis

A Hewlett Packard 5890 series-II gas chromatograph fitted with an electron capture detector and a DB-1 capillary column was used for analysis of volatile halogenated compound HCA. Column dimensions were 20 mm×0.18 mm×0.4 um; Column phase: 100% methyl siloxane. All injections were made with an auto-injector (HP 7673) (0.5 µl volume of sample), and the solvent for all injected samples was hexane. Column temperature was initially 30° C. for 2.00 min., then ramped to 175° C. at 6.00° C./minute and then ramped to 275° C. at 10.0° C./minute and held for 2.00 minutes. The results of these studies are shown in Tables 2, 3, and 4.

TABLE 2

ANTIOXIDANT ACTIVITIES IN RED AND WHITE WINE
Inglenook Red (Burgundy) and White wines were taken for testing. After partial purification, both samples were checked for antioxidant activity as described in the methods.

| Sample | Relative Act. at native pH | Specific Act. | Relative Act. at pH 9.0 | Specific Act. |
|---|---|---|---|---|
| Red Wine | 0% | 0 | 80% | $3.44 \times 10^5$ |
| White Wine | 0% | 0 | 0% | 0 |

Note:
Specific Activity is expressed as "moles HCA degraded/hour/ml of antioxidant"
The native pH of red wine was pH 3.3 and that of white wine was pH 3.1. The pH in both cases was brought to pH 9.0 with sodium hydroxide.
Ascorbate had no effect on the activity.
Relative activity is the activity of the sample relative to the activity of the buffer control

TABLE 3

ANTIOXIDANT ACTIVITIES IN COMMERCIAL VEGETABLE AND FRUIT JUICES
Store bought fruit and vegetable juices were taken for testing. After partial purification, the samples were checked for antioxidant activity as described in the methods. It is present in six juices that are purported to be have good antioxidant benefits.

| Sample (Native ph) | Rel Act at Native pH | Spec Act | Rel Act at pH 9.0 | Spec Act |
|---|---|---|---|---|
| Welch's Grape juice (3.3) | 0% | 0 | 30% | $1.29 \times 10^5$ |
| Weichade Orange juice (3.3) | 32% | $1.38 \times 10^5$ | 54% | $2.30 \times 10^5$ |
| Mott's Apple juice (3.5) | 35% | $1.51 \times 10^5$ | 100% | $4.30 \times 10^5$ |
| Kroger Vegetable juice (4.2) | 0% | 0 | 60% | $2.60 \times 10^5$ |
| Libby's Banana juice (3.7) | 0% | 0 | 80% | $3.44 \times 10^5$ |

TABLE 3-continued

ANTIOXIDANT ACTIVITIES IN COMMERCIAL VEGETABLE AND FRUIT JUICES

Store bought fruit and vegetable juices were taken for testing. After partial purification, the samples were checked for antioxidant activity as described in the methods. It is present in six juices that are purported to be have good antioxidant benefits.

| Sample (Native ph) | Rel Act at Native pH | Spec Act at Native pH | Rel Act at pH 9.0 | Spec Act at pH 9.0 |
|---|---|---|---|---|
| Hollywood's Carrot juice (6.0) | 47% | $2.02 \times 10^5$ | 60% | $2.60 \times 10^5$ |

Note:
Rel. Act. = Relative Activity; Spec. Act. = Specific Activity
Specific Activity is expressed as "moles HCA degraded/hour/ml of antioxidant"
The native pH of the juices ranged from pH 3.3 to pH 6.0. The pH in all cases was brought to pH 9.0 with sodium hydroxide.
Ascorbate had no effect on the activity.
Relative activity is the activity of the sample relative to the activity of the buffer control

TABLE 4

ANTIOXIDANT ACTIVITIES TN COMMERCIAL NUTRITIONAL SUPPLEMENTS

Four popular health food supplements were chosen for this study. After extracting and partial purification, they were tested for antioxidant activity as described in the methods. The extraction buffer brought the pH of the samples to pH 9.0. One third of the recommended daily dose, of each brand, was taken for the test.

| Sample | Relative Activity | Specific Activity |
|---|---|---|
| Nature's Plus | 100% | $4.30 \times 10^5$ |
| Amway's Double X | 100% | $4.30 \times 10^5$ |
| Nature's Secret - Morning & Evening MultiPlus | 40% | $1.72 \times 10^5$ |
| Juice Plus | 85% | $3.66 \times 10^5$ |

Note:
Specific Activity is expressed as "moles HCA degraded/hour/ml of antioxidant"
The pH in all cases was brought to pH 9.0 with sodium hydroxide.
Ascorbate had no effect on the activity.

TABLE 4-continued

ANTIOXIDANT ACTIVITIES TN COMMERCIAL NUTRITIONAL SUPPLEMENTS

Four popular health food supplements were chosen for this study. After extracting and partial purification, they were tested for antioxidant activity as described in the methods. The extraction buffer brought the pH of the samples to pH 9.0. One third of the recommended daily dose, of each brand, was taken for the test.

| Sample | Relative Activity | Specific Activity |
|---|---|---|

Relative activity is the activity of the sample relative to the activity of the buffer control

EXAMPLE 3

Determination Molecular Weight and Amino Acid Sequence

A sample was collected for mass spectral analyses. The peak with a retention volume of 18, 19 and 20 ml was collected, pooled and submitted for analyses. The MALDI spectrum was obtained by the Chemistry Department, University of Georgia, Athens Ga. Although the spectrum was weak, the molecular weight was estimated to be 1141 Da.

A purified sample of the antioxidant was obtained for sequencing by collecting samples of the eluted peak off the FPLC. This was then subjected to gel electrophoresis and transferred to PVDP. The sequencing was carried out at the Molecular Genetics Instrumentation Facility, University of Georgia, Athens Ga., using PVDF membrane buffer. The partial amino acid sequence for this peptide was fourteen amino acids in length is shown in SEQ ID NO: 1.

SEQ ID NO: 1 M, P, L, X, E, K, G, L, D, X/G, A, T/K, X, X

It is to be understood that X in SEQ ID NO: 1 may be any naturally occurring amino acid. In a preferred embodiment, one or more Xs is a methionine. The designations X/G and T/K indicate that either X or G, or T or K may be present at the indicated positions.

It should be understood that the foregoing relates only to a preferred embodiment of the present invention and that numerous modifications or alterations may be made therein without departing from the spirit and the scope of the invention as set forth in the appended claims.

The invention claimed is:

1. An isolated peptide having antioxidant activity comprising the amino acid sequence set forth in SEQ ID NO: 1 or a conservative modified variation thereof;

wherein X is any naturally occurring amino acid.

2. The peptide of claim 1, wherein the peptide comprises an amino acid sequence set forth in SEQ ID NO: 2, SEQ ID NO: 3, SEQ ID NO: 4, SEQ ID NO: 5, SEQ ID NO: 6, or SEQ ID NO: 7.

3. The peptide of claim 1, wherein X is methionine.

4. A peptide isolated from a plant comprising the amino acid sequence set forth in SEQ ID NO: 1, wherein the peptide is characterized by the properties of being soluble in methanol, protease resistant, heat stable, having a molecular weight of approximately 1.2 KDa, and displaying UV/visible absorption spectrum maxima at about 216 nm and 270 nm.

5. The peptide of claim 4, wherein the peptide dehalogenates tetrachloroethylene (PCE), trichloroethylene (TCE), pentachlorophenol (PCP), trichlorobenzene (TCB), dichlorobenzene, carbon tetrachloride (CTC), toxaphene or dichloro-diphenyl-trichloroethane (DDT), such dehalogenase activity being inhibited by EDTA.

6. The peptide of claim 4, wherein the plant is Elodea or hay.

7. A method of increasing the antioxidant properties of a substance comprising adding to the substance a peptide having antioxidant activity and the amino acid sequence SEQ ID NO: 1, or a conservative modified variation thereof;

wherein X is any naturally occurring amino acid.

8. The method of claim 7, wherein the substance is a food, beverage, nutritional supplement, vitamin, herbal extract, cosmetic, pharmaceutical, or tobacco product.

9. The method of claim 8 further comprising addition of a molecule which acts as an electron source.

10. The method of claim 7, wherein the peptide contains an amino acid sequence set forth in SEQ ID NO: 2, SEQ ID NO: 3, SEQ ID NO: 4, SEQ ID NO: 5, SEQ ID NO: 6, or SEQ ID NO: 7.

11. The method of claim 7, wherein X is methionine.

12. A method of isolating a peptide from a plant comprising:
   homogenizing a sample of the plant in a buffer to produce a homogenate;
   filtering the homogenate to obtain a filtrate;
   centrifuging the filtrate to obtain a supernatant;
   purifying the supernatant through precipitation by lowering the pH value;
   raising pH of the supernatant with base;
   centrifuging the supernatant;
   filtering the supernatant through a filter to obtain a second filtrate; and
   concentrating on the second filtrate;
   wherein the peptide is methanol soluble, protease resistant, heat stable, has a molecular weight of approximately 1.2 KDa, and displays UV/visible absorption spectrum maxima at about 216 nm and 270 nm.

13. The method of claim 12 further compromising: lyophilizing the second filtrate to obtain a lyophilized product;
   resuspending the lyophilized product in methanol to obtain a solution free of water soluble components;
   lyophilizing the solution to obtain a powder;
   resuspending the powder in a buffer;
   and chromatographically purifying the powder dissolved in the buffer solution.

14. The method of claim 12, wherein the peptide dehalogenates PCE, TCE, PCP TCB, DCB, CTC, toxaphene or DDT, such dehalogenase activity being inhibited by EDTA.

15. The method of claim 12, wherein the plant is Elodea or hay.

* * * * *

SEQUENCE LISTING

```
<160> NUMBER OF SEQ ID NOS: 7

<210> SEQ ID NO 1
<211> LENGTH: 14
<212> TYPE: PRT
<213> ORGANISM: Elodea sp.
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid or Glycine
<220> FEATURE:
<221> NAME/KEY: MISC_FEATURE
<222> LOCATION: (12)..(12)
<223> OTHER INFORMATION: X = Threonine or Lysine
<220> FEATURE:
<221> NAME/KEY: MISC_FEATURE
```

-continued

```
<222> LOCATION: (13)..(14)
<223> OTHER INFORMATION: X = any amino acid

<400> SEQUENCE: 1

Met Pro Leu Xaa Glu Lys Gly Leu Asp Xaa Ala Xaa Xaa Xaa
1               5                   10

<210> SEQ ID NO 2
<211> LENGTH: 14
<212> TYPE: PRT
<213> ORGANISM: Elodea sp.
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (12)..(12)
<223> OTHER INFORMATION: X = Threonine or Lysine
<220> FEATURE:
<221> NAME/KEY: MISC_FEATURE
<222> LOCATION: (13)..(14)
<223> OTHER INFORMATION: X = any amino acid

<400> SEQUENCE: 2

Met Pro Leu Xaa Glu Lys Gly Leu Asp Gly Ala Xaa Xaa Xaa
1               5                   10

<210> SEQ ID NO 3
<211> LENGTH: 14
<212> TYPE: PRT
<213> ORGANISM: Elodea sp.
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid or Glycine
<220> FEATURE:
<221> NAME/KEY: MISC_FEATURE
<222> LOCATION: (13)..(14)
<223> OTHER INFORMATION: X = any amino acid

<400> SEQUENCE: 3

Met Pro Leu Xaa Glu Lys Gly Leu Asp Xaa Ala Lys Xaa Xaa
1               5                   10

<210> SEQ ID NO 4
<211> LENGTH: 14
<212> TYPE: PRT
<213> ORGANISM: Elodea sp.
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid or Glycine
<220> FEATURE:
<221> NAME/KEY: MISC_FEATURE
<222> LOCATION: (13)..(14)
<223> OTHER INFORMATION: X = any amino acid

<400> SEQUENCE: 4

Met Pro Leu Xaa Glu Lys Gly Leu Asp Xaa Ala Thr Xaa Xaa
1               5                   10

<210> SEQ ID NO 5
```

-continued

```
<211> LENGTH: 14
<212> TYPE: PRT
<213> ORGANISM: Elodea sp.
<220> FEATURE:
<221> NAME/KEY: MISC_FEATURE
<222> LOCATION: (4)..(14)
<223> OTHER INFORMATION: X = any amino acid

<400> SEQUENCE: 5

Met Pro Leu Xaa Glu Lys Gly Leu Asp Gly Ala Thr Xaa Xaa
1               5                   10

<210> SEQ ID NO 6
<211> LENGTH: 14
<212> TYPE: PRT
<213> ORGANISM: Elodea sp.
<220> FEATURE:
<221> NAME/KEY: MISC_FEATURE
<222> LOCATION: (4)..(14)
<223> OTHER INFORMATION: X = any amino acid

<400> SEQUENCE: 6

Met Pro Leu Xaa Glu Lys Gly Leu Asp Gly Ala Lys Xaa Xaa
1               5                   10

<210> SEQ ID NO 7
<211> LENGTH: 14
<212> TYPE: PRT
<213> ORGANISM: Elodea sp.
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid or Glycine
<220> FEATURE:
<221> NAME/KEY: MISC_FEATURE
<222> LOCATION: (13)..(14)
<223> OTHER INFORMATION: X = any amino acid

<400> SEQUENCE: 7

Met Pro Leu Xaa Glu Lys Gly Leu Asp Xaa Ala Thr Xaa Xaa
1               5                   10
```